United States Patent [19]

Celmer et al.

[11] Patent Number: 4,552,843
[45] Date of Patent: Nov. 12, 1985

[54] PROCESS FOR PRODUCING AN ACIDIC POLYCYCLIC ETHER ANTIBIOTIC BY CULTIVATION OF A NOVEL STRAIN OF *STREPTOMYCES ENDUS* SUBSPECIES *AUREUS*

[75] Inventors: Walter D. Celmer, New London; Walter P. Cullen, East Lyme, both of Conn.; Hiroshi Maeda, Aichi; Junsuke Tone, Chita, both of Japan

[73] Assignee: Pfizer Inc., New York, N.Y.

[21] Appl. No.: 581,384

[22] Filed: Feb. 17, 1984

[51] Int. Cl.[4] .................. C12P 19/62; C12P 17/18; C12N 1/20; C12R 1/465
[52] U.S. Cl. ................... 435/76; 435/119; 435/253; 435/886
[58] Field of Search ............ 435/74, 75, 76, 253, 435/886, 118, 119

[56] References Cited

U.S. PATENT DOCUMENTS 4,269,971  5/1981  Yamagishi et al. .......... 536/17 R
4,361,649 11/1982  Celmer et al. ............. 435/119

FOREIGN PATENT DOCUMENTS 57-4975  1/1982  Japan ........................ 435/121

OTHER PUBLICATIONS

Hamill et al., J. Antibiotics, 22, 161 (1969).
Mizutani et al., J. Antibiotics, 33, 137 (1980).
Agtarap et al., J. Amer. Chem. Soc., 89, 5737 (1967).
Nakano et al., J. Antibiotics, 35, 760 (1982).
Miyazaki et al., J. Antibiotics, 27, 814 (1974).

*Primary Examiner*—Thomas G. Wiseman
*Assistant Examiner*—Jean A. Heck
*Attorney, Agent, or Firm*—Charles J. Knuth; Albert E. Frost; Paul D. Thomas

[57] ABSTRACT

A new acidic polycyclic ether antibiotic, CP-63,517, having the formula:

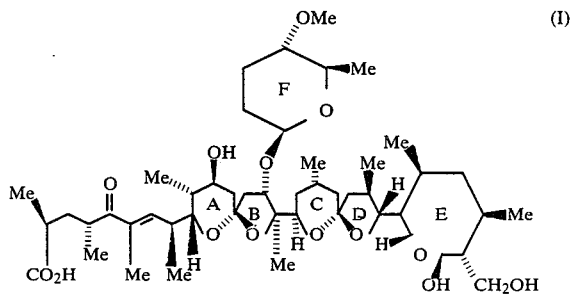

and cationic salts thereof produced by submerged aerobic propagation of *Streptomyces endus* subsp. *aureus*, ATCC-39574, a new strain of microorganism isolated from a soil sample in Japan, a process for producing this antibiotic and methods for its use to improve feed utilization, promote growth of cattle and swine and to control coccidiosis.

4 Claims, No Drawings

PROCESS FOR PRODUCING AN ACIDIC POLYCYCLIC ETHER ANTIBIOTIC BY CULTIVATION OF A NOVEL STRAIN OF *STREPTOMYCES ENDUS* SUBSPECIES *AUREUS*

BACKGROUND OF THE INVENTION

This invention relates to a new antibiotic substance, designated as CP-63,517, which was isolated from fermentation of a new strain of the genus Streptomyces isolated from a soil sample collected in Okayama Prefecture, Japan and assigned the code number N497-34. Structurally the new antibiotic of this invention is a new member of the acidic polycyclic ether (ionophore) antibiotics. This family of antibiotics includes dianemycin [*J. Antibiotics*, 22, 161 (1969)] and ibid., 33, 137 (1980); monensin [*J. Amer. Chem. Soc.*, 89, 5737 (1967)]; salinomycin [*J. Antibiotics*, 27, 814 (1974)]; Antibiotic TM-531 disclosed in U.S. Pat. No. 4,269,971 and Antibiotic 53,607 disclosed in U.S. Pat. No. 4,361,649.

SUMMARY OF THE INVENTION

The invention provides a new acidic polycyclic ether antibiotic substance designated CP-63,517 having the chemical formula

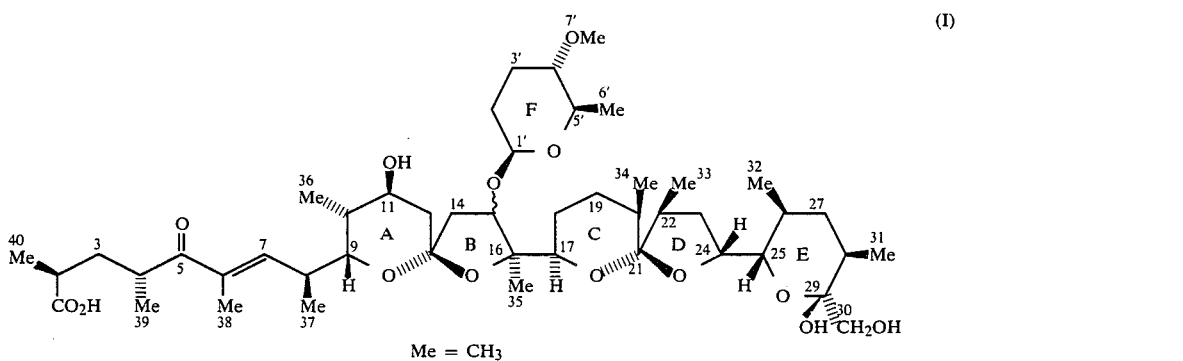

(I)

Me = CH₃ and pharmaceutically acceptable cationic salts thereof which are active against a variety of microorganisms and are effective in controlling coccidiosis, enteritis, swine dysentery and theileriosis as well as being effective in promotion of growth in swine and ruminants; and to promote increased efficiency of feed utilization in swine and cattle.

CP-63,517 has been isolated by culture of a new strain isolated from a soil sample collected in Okayama Prefecture, Japan. Said strain was designated N497-34 and has been identified as a new strain of *Streptomyces endus*, subsp. *aureus*. It is now on deposit with American Type Culture Collection under Accession No. 39574.

Also provided in this invention are: a method of increasing the efficiency of feed utilization in swine and cattle by means of the antibiotic of formula (I) or a pharmaceutically acceptable salt thereof; an improved nutrient feed composition for cattle or swine which incorporates said antibiotic or its salts; a process for production of the antibiotic CP-63,517 or a pharmaceutically acceptable salt thereof by cultivating said new strain of *Streptomyces endus* subsp. *aureus* in an aqueous culture medium; and a biologically pure culture of said new strain of the species *Streptomyces endus* subsp. *aureus*, ATCC-39574.

DETAILED DESCRIPTION OF THE INVENTION

The antibiotic substance of the present invention is produced by fermentation of a strain, designated N497-34, which was isolated from a soil sample collected in Okayama Prefecture, Japan. Culture N497-34 was characterized and identified by Liang H. Huang, PhD., Central Research, Pfizer Inc., Groton, Conn., U.S.A. as described hereinbelow.

On examination, culture N497-34 was recognized as a Streptomyces species because of the narrow dimensions of the hyphae, production of aerial mycelium and spores borne in chains on the aerial mycelium.

The culture N497-34 was planted from a slant into ATCC No. 172 broth and grown for four days at 28° C. on a shaker. It was then centrifuged for 20 minutes, washed three times with sterile distilled water and planted on media commonly used for identification of members of the Actinomycetales.

The culture was incubated at 28° C., and the results read at varying times but most commonly were taken at 14 days. The colors were described in common terminology, but exact colors were determined by comparisons with color chips from the Color Harmony Manual, fourth edition. The methods of whole-cell amino acid and sugar analyses are those described in Becker et al., *Appl. Microbiol.*, 12, 421–423 (1964); and in Lechevalier, *J. Lab. Clin. Med.*, 71, 934–944 (1968). For the comparison purpose, *Streptomyces endus* subsp. *aureus* NRRL 12174 was obtained from Northern Regional Research Center (NRRC), U.S.D.A., Peoria, Ill.

Identification media used for the characterization of the culture and references for their composition are as follows:

1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.

11. Nutrient Agar—Ibid, medium no. 14, p. 330.
12. Gordon and Smith's Tyrosine Agar—R. E. Gordon and M. M. Smith, *J. Bact.,* 69, 147–150 (1955).
13. Casein Agar—Ibid.
14. Calcium Malate Agar—S. A. Waksman, *Bact. Rev.,* 21, 1–29 (1957).
15. Gelatin—R. E. Gordon and J. M. Mihm, *J. Bact.,* 73, 15–27 (1957).
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M. P. Lechevalier, *J. Lab. and Clinical Med.,* 71, 934–944 (1968), but use only 30 g potatoes, 2.5 g carrots and 20 g agar.
20. 2% Tap Water Agar.
21. Skim Milk—Difco.
22. Cellulose utilization—
    (a) H. L. Jensen, *Proc. Linn. Soc. N.S.W.,* 55, 231–248 (1930).
    (b) M. Levine and H. W. Schoenlein, A Compilation of Culture media, medium no. 2511, 1930.
23. Carbohydrates—ISP #9 medium, Difco.
24. Temperature Range—ISP #2 medium plus 50 ml of coconut milk per liter of the medium.

Culture N497-34 exhibited the following characteristics, with colors and whole-cell amino acid and sugar analyses determined by the above-mentioned methods.

Yeast Extract-Malt Extract Agar—Growth good, white, pale yellow to pale pink gray (lea, 1 ½ca, near gray series 3dc, 5dc, 5fe), raised, wrinkled, aerial mycelium same as surface; reverse brown (2pg, 3ne); soluble pigment yellowish brown (21c, 3nc).

Oatmeal Agar—Growth moderate to good, off-white, gray to pink gray (near gray series 3fe, 5fe, 7fe, 7ih), slightly raised, smooth, velvet, aerial mycelium same as surface; reverse pale yellow (2ca) to gray (near gray series 3dc, 3fe); soluble pigment pale yellowish to yellowish (1½ea, 1½ga).

Inorganic Salts-Starch Agar—Growth moderate to good, whitish yellow to pink gray (1½ca, near gray series 1ba, 5fe, 7fe, 7ih), raised, wrinkled, aerial mycelium same as surface; reverse yellowish to pink gray (1½ga, near gray series 5fe); soluble pigment yellowish (1½ga, 1½ea).

Glycerol-Asparagine Agar—Growth poor to moderate, off-white (near gray series 2ba), thin, smooth, or appearing as isolated colonies, aerial mycelium off-white; reverse colorless to pale yellowish (1½ca); no soluble pigment.

Czapek-Sucrose Agar—Growth moderate, pale off-white (near 1½ca, near gray series 2cb), thin, smooth, with circular or curved lines, no aerial mycelium; reverse cream (1½ca); soluble pigment cream (1½ca).

Glucose-Asparagine Agar—Growth good, gray, pink gray (near gray series 3fe, 5fe) to yellowish (lea, 1ga), moderately raised, wrinkled or granular, aerial mycelium same as surface; reverse yellowish gray to gray (2gc, 2ge, near gray series 3fe, 3ih); soluble pigment yellowish (1½ia, 1½la).

Gordon and Smith's Tyrosine Agar—Growth moderate, off-white (near gray series 2ba), moderately raised, wrinkled, or appearing as isolated colonies, aerial mycelium off-white; reverse pale yellow (1½ca, 1½ea); soluble pigment pale yellow (2ea).

Calcium Malate Agar—Growth moderate, white to off-white (near gray series 1ba), thin, smooth, or appearing as isolated colonies; aerial mycelium sparse, white to off-white; reverse cream (1½ca); soluble pigment cream (1½ca).

Casein Agar—Growth good, white to pale grayish cream (near 2ec, 3ec), moderately raised, finely wrinkled, no aerial mycelium; reverse pale lavender (3ec); soluble pigment pale lavender (4ec).

Bennett's Agar—Growth good, white, pale yellow to pink gray (lea, near gray series 5fe, 7fe, 7ih), raised, wrinkled, aerial mycelium same as surface; reverse lavender gray (4ig, 4li, 5ig, 5li); soluble pigment yellowish (1½na).

Emerson Agar—Growth good, white to off-white, raised, wrinkled, or appearing as isolated colonies, with white to off-white aerial mycelium; reverse yellowish brown (2ea, 2lc); soluble pigment brown (3lc).

Nutrient Agar—Growth moderate, white, wrinkled, raised, or appearing as isolated colonies, aerial mycelium white; reverse cream (1½ca); no soluble pigment.

Gelatin Agar—Growth good, white to cream (1½ca), moderately raised, wrinkled, aerial mycelium white; reverse cream (2ca); no soluble pigment.

Starch Agar—Growth good, white, raised, wrinkled, aerial mycelium white; reverse pale yellowish to yellowish brown (2ea, 2ic); soluble pigment cream (2ca).

Potato Carrot Agar—Growth moderate, gray to pink gray (near gray series 3fe, 5fe, 7fe, 7ih), velvet, raised at the center but thin toward the edge, smooth, aerial mycelium same as surface; reverse pink gray (near gray series 5fe, 5ih); soluble pigment cream (1½ca).

Tap Water Agar—Growth moderate to good, gray to pink gray (near gray series 3fe, 5fe, 5ih); appearing as raised, isolated, velvet colonies; aerial mycelium gray to pink gray; reverse gray to dark gray (near gray series 5ih, 3ih, 3ml); no soluble pigment.

Morphological Properties—The morphological properties were observed on oatmeal agar after 14 days of incubation: spore mass in Gray color-series; sporophores monopodially branched; spore chains spiral, of small diameter (3 to 4 μm), slightly open, 3 to 7 turns per spore chain, 10 to 50 spores per spore chain; spore short rod-shaped, sometimes globose, oval or elliptical, straight or slightly curved, with some of the slightly curved ones having non-parallel ends and thus appearing five-angled, 1.0–1.8×0.9–1.2 μm or 0.9–1.2 μm in diameter; warty, as revealed by scanning electron microscopy.

Biochemical Properties—Melanin not produced; hydrogen sulfide produced; gelatin liquefied; starch hydrolyzed; nitrate reduced to nitrite; good growth on Levine and Schoenlein's cellulose broth but poor growth on Jensen's cellulose broth; no decomposition on both cellulose broths; coagulation and clearing on milk; casein digestion positive; calcium malate digestion positive; tyrosine digestion negative. Carbohydrate utilization: glucose, arabinose, fructose, inositol, mannitol, raffinose, rhamnose, sucrose, and xylose all utilized.

| Temperature Relations | | | |
| --- | --- | --- | --- |
| 21° C. | 28° C. | 37° C. | 45° C. |
| Good Growth | Excellent Growth | Good Growth | Moderate Growth |

On cell wall analyses of culture N497-34 it was found that the whole-cell hydrolysates contained LL-diaminopimelic acid but no characteristic sugars. Culture N497-34 is characterized by gray color of spores in mass, negative melanin reaction, spiral spore chains, and spores with a warty surface. These features and the results of whole-cell analyses place the culture in the genus Streptomyces. When compared with descriptions of known species of Streptomyces reported in the literature, it closely resembles *S. endus* Anderson & Gottlieb subsp. *aureus* Tomita, Nakano, Sato, Shirahata, Yoshida & Morimoto NRRL 12174, as described in *Japan Kokai Tokkyo Koho*, No. 57-4975, published Jan. 11, 1982. The latter was obtained from NRRL and was compared side by side with N497-34. Except for the fact that N497-34, but not NRRL 12174, grows at 45° C. and coagulates milk, both cultures share the same biochemical and physiological properties. On ISP #2 medium, ISP #4 medium and Bennett's agar, culture N497-34 produces more pink-gray aerial mycelium without yellow exudate; its colonies on ISP #5 medium and nutrient agar are smaller; its colonies on Czapek-sucrose agar show cream lines or circles; its colonies on glucose-asparagine are pink-gray rather than white to cream and produce yellow rather than no soluble pigment. These cultural variations are minor and may occur among different strains of a species of Streptomyces. The culture N497-34 is therefore considered as a new strain of *Streptomyces endus* Anderson & Gottlieb subsp. *aureus* Tomita, Nakano, Sato, Shirahata, Yoshida & Morimoto. It has been deposited with the American Type Culture Collection, 12301 Parklawn Dr., Rockville, Md. 20852, U.S.A. under the provisions of the Budapest Treaty on Jan. 10, 1984, under Accession No. ATCC-39574. The permanency of the deposited culture N497-34 at the American Type Culture Collection is guaranteed throughout the effective life of any patent granted on this application; access to culture N497-34 is available during pendency of this application to one determined by the Commissioner of Patents and Trademarks to be entitled thereto under 35 USC 122 and 37 CFR 1.14; and all restrictions on the availability of the deposited culture will be removed irrevocably on the granting of a patent on this application.

The novel antibiotic substance of this invention is obtained by fermenting the new strain of *Streptomyces endus* subsp. *aureus*, ATCC-39574 and extraction of the whole broth at natural pH with methylisobutyl ketone and concentration of the solvent to a viscous oil. The oil was suspended in heptane and batch treated with silica gel. The silica gel cake was eluted with chloroform, chloroform/ethyl acetate, ethyl acetate and ethyl acetate/acetone. After concentration, the ethyl acetate fraction yielded a small amount of crude product from which Antibiotic CP-63,517 was crystallized as the mixed sodium/potassium salt.

The *Streptomyces endus* subsp. *aureus* ATCC-39574 can be grown at a temperature of from 24° to 36° C. under submerged conditions with agitation and aeration on media consisting of carbohydrate sources such as sugars, starches, glycerol; organic nitrogen substances such as soybean meal, casamino acids, yeast extract; growth substance such as grain solubles, fish meal, cotton seed meal; mineral salts containing trace elements such as iron, cobalt, copper, zinc and calcium carbonate or phosphates as buffering agents. The antibiotic can be recovered by extracting the whole broth with various organic solvents, e.g., n-butanol, methylisobutyl ketone, or chloroform, at pH within the range of from 4.0 to 8.0, or separating the mycelium after growth has been completed, and extracting the mycelium; the filtrate being discarded. The extract is concentrated to a thin syrup, dissolved in heptane, e.g., and chromatographed on silica gel to obtain the pure compound.

Inoculum is prepared by scraping vegetative cells from slants or Roux bottles inoculated with the ATCC-39574 culture. A solid medium suitable for initial growth on slants and Roux bottles is ATCC medium No. 172.

| ATCC 172 | |
|---|---|
| Ingredient | Grams/liter |
| Glucose | 10 |
| Soluble Starch | 20 |
| Yeast Extract | 5 |
| NZ Amine A* | 1 |
| Calcium Carbonate | 1 |
| Distilled Water to 1000 ml; pH to 7.0 with KOH Add Agar | 20 |

*Registered trademark for enzymatic digest of casein, Humko Sheffield Chemical Co., Inc.

Vegetative cells from slants are used to inoculate either shake flasks or inoculum tanks; or alternately the inoculum tanks are inoculated from shake flasks. In shake flasks growth will generally have reached its maximum in 96 to 120 hours whereas in the inoculum tanks growth will usually be at the most favorable period in 72 to 96 hours. A fermentor is inoculated with vegetative broth from the inoculum flasks or tank under completely aseptic conditions and fermented for a period of 48 to 120 hours. Aeration is maintained in the shake flask by agitation on a shaker or in tanks by forcing sterile air through a sparger at the rate of $\frac{1}{2}$ to 2 volumes of air per volume of broth per minute. The speed of agitation (stirring) depends upon the type of agitator employed; a shake flask is usually run at 150 to 200 cycles per minute (CPM) and a fermentor at 300 to 1700 revolutions per minute (RPM). Sterility must be maintained at all times. The temperature is regulated between 28° to 36° C. Foaming during the fermentation can be controlled with sterile antifoams, e.g., refined soybean oil or other suitable antifoaming agent added to the makeup or to the fermentor aseptically as needed after inoculation.

Shake flasks are prepared using one of the following media:

| Ingredient | Grams/liter |
|---|---|
| CL13MZ | |
| Glucose | 20 |
| Soy Flour | 10 |
| NZ Amine YTT* | 5 |
| Sodium Sulfate | 0.5 |
| Cobalt Chloride | 0.002 |
| Calcium Carbonate | 2 |
| Water to 1 liter pH 6.9-7.0 | |
| JDY TT | |
| Cerelose | 10 |
| Corn Starch | 5 |
| Corn Steep Liquor | 5 |
| NZ Amine YTT* | 5 |
| Cobalt Chloride | 0.002 |
| Calcium Carbonate | 3 |
| Water to 1 liter pH 6.9-7.0 | |

*Registered trademark for enzymatic digest of casein, Humko Sheffield Co., Inc.

One hundred ml of medium is distributed into 300 ml shake flasks and sterilized at 120° C. and 15 p.s.i. (1.07 kg/cm$^2$) for 30 minutes. After cooling, the medium is inoculated with a vegetative cell suspension from the *S. endus* subsp. *aureus* slant culture ATCC-39574 grown on ATCC 172 medium in agar. The flasks are shaken at 28° C. on a rotary shaker having a displacement of 1.5 to 2.5 inches (3.8–5.1 cm) and 150 to 200 CPM for three to four days. One flask is used to inoculate a five liter fermentation vessel containing three liters of one of the following media: CN-2 (below), or CL13MZ or JDY TT (above).

| CN-2 | |
|---|---|
| Ingredient | Grams/liter |
| Cerelose | 10 |
| Corn Starch | 10 |
| Soybean Flour | 10 |
| NZ Amine YTT* | 10 |
| Cobalt Chloride | 0.002 |
| Calcium Carbonate | 1 |

*Registered trademark for enzymatic digest of casein, Humko Sheffield Co., Inc.

One milliliter of an antifoaming agent was added, then the vessels were sealed and sterilized at 120° C. and 15 p.s.i. (1.07 kg per cm$^2$) for 45 minutes. The pots were inoculated with one (about 3% inoculum) flask, fermented for 96 to 144 hours at 30° C., stirred at 1700 RPM with an air rate of one volume of air per volume of liquid per minute.

When the fermentation was completed (based on an antibiotic disc assay versus *B. subtilis* ATCC 6633), the fermentors were stopped, filtered at the natural pH with the aid of a filter aide, for example, Celite. The filter cake was slurried in methanol, concentrated in vacuo, diluted with 2–3 volumes of water, then extracted twice with $\frac{1}{3}$ to $\frac{1}{2}$ volume of a water immiscible solvent such as methylisobutyl ketone or n-butanol. The solvent layer was separated from the aqueous phase by aspiration or centrifugation, filtered, and the filtrate concentrated in vacuo to a viscous oil.

The bioactivity of the broth, and subsequent recovery streams can be followed by using a sensitive strain of *Bacillus subtilis* ATCC 6633 or *Staphylococcus aureus* ATCC 6538. The components in the broth and recovery streams can be visualized by thin-layer chromatography (tlc) using silica gel≠ plates in neat ethyl acetate. The developed plates are sprayed with vanillin reagent (3 g vanillin in 75 ml ethanol and 25 ml 85% phosphoric acid) and heated to 80° C. The antibiotic CP-63,517 appears as a greenish spot. The developed tlc plate can also be overlayed with agar seeded with either *S. aureus* or *B. subtilis* to which tetrazolium dye* has been added and incubated at 37° C. for 16 hours to visualize the antibiotic (white against a pink background).

≠ Silica gel G (70-230M ASTM) E. Merck.
*2,3,5 Triphenyl-2H tetrazolium chloride monohydrate, 98% Aldrich Chemical Co., Inc. T-8485-9.

Scale-up in large fermentors was carried out by preparing shake flasks containing 0.7 liters of CL13MZ or JDY TT medium. The shake flask inoculum was fermented for 3 to 5 days at 28° C. and used to inoculate a 50 or 1700 gallon (190 or 6540 liter) fermentor containing 25 or 1200 gallons (96 or 4600 liters) of JDY TT medium. Approximately one liter of inoculum was used in the tank. The fermentor, after fermenting 5 to 7 days, was harvested to yield about 25 or 1100 gallons (96 or 4230 liters), respectively. The whole broth was extracted with 1/5 volume of methylisobutyl ketone at natural pH, separated on an Alpha DeLaval separator or a Podbielniak extractor and the solvent concentrated in vacuo to an oil. The oil was further concentrated to a syrup, which was suspended in heptane, stirred with silica gel, filtered thru a bed of silica gel and washed gel and washed repeatedly with heptane. The antibiotic was eluted stepwise with chloroform, chloroform/ethyl acetate, ethyl acetate and finally 50% acetone in ethyl acetate. The elution was followed by thin layer chromatography and bioassay of the fractions. The active cuts were combined, concentrated and rechromatographed to isolate the antibiotic CP-63,517. Passage of the active eluates through a granular carbon column removed interfering materials and improved the recovery such that crystalline CP-63,517 was recovered.

The antibiotic compound of this invention of formula (I) is acidic, and it will form cationic salts by reaction with basic agents. All such salts are within the scope of this invention. These salts are prepared by conventional methods for polyether (ionophore) antibiotics. In one method, a solution of the compound of formula (I) in a volatile, water immiscible, organic solvent is washed with an aqueous solution containing at least a stoichiometric equivalent, and preferably a large excess, of an appropriate basic agent. After drying the organic solvent solution it is evaporated in vacuo to give the desired cationic salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

Antibiotic CP-63,517 exhibits inhibitory action against the growth of a number of Gram-positive microorganisms. In Table I, below, the results of in vitro MIC tests are summarized. For this test each organism is inoculated in a series of test tubes of CP-63,517 to determine the minimal concentration of the antibiotic in mcg/ml which inhibits the growth of the organism over a period of 24 hours (MIC).

Swine dysentery is one of the most common swine diseases diagnosed in the United States. Additionally, the disease is prevalent in many other countries and annually causes many thousands of dollars losses in stock to swine growers around the world. It has recently been discovered that a large spirochete is the causative organism of the disease. This organism, *Treponema hyodysenteriae*, has now been isolated and shown to be capable of producing the disease [Harris, D. L. et al.: "Swine Dysentery-1 Inoculation of Pigs with Treponema hyodysenteriae (New Species) and Reproduction of the Disease," *Vet. Med/SAC*, 67: 61–64: 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

TABLE I

| Organism | | CP-63,517 MIC mcg/ml |
|---|---|---|
| *Staphylococcus aureus* | 01A005 | 0.39 |
| | 01A052 | 0.39 |
| | 01A110 | 0.39 |
| | 01A106 | 0.78 |
| | 01A539 | 0.78 |
| | 01A543 | 3.12 |
| *Staphylococcus epidermidis* | 01B087 | 0.78 |

TABLE I-continued

| Organism | | CP-63,517 MIC mcg/ml |
|---|---|---|
| | 01B111 | 0.39 |
| Streptococcus pyogenes | 020054 | 0.10 |
| Erysip. rhusio | 04A005 | 0.39 |
| Lactobacillus casei | 09B001 | 0.39 |
| L. catenaforme | 09C001 | 0.39 |
| Corynebacterium pyogenes | 11D001 | 12.5 |
| | 11D002 | 12.5 |
| | 11D003 | 12.5 |
| Peptococcus sp. | 17B001 | ≦0.10 |
| Haemophilus parahemol. | 54B002 | 25 |
| Pasteurella multocida | 59A013 | 50 |
| | 59A048 | 0.39 |
| P. haemolytica | 59B018 | 0.39 |
| | 59B046 | 0.39 |
| | 59B061 | 50 |
| Bordatella bronchi | 73A006 | 0.39 |
| | 73A016 | 6.25 |
| Bacteroides vulgates | 78E032 | 25 |
| Fusobacterium plauti | 84G001 | 0.39 |
| F. necrophorum | 84C004 | 25 |
| Moraxella bovis | 93A001 | 50 |
| Treponema hyodysenteriae | 94A001 | 6.25 |
| | 94A002 | 6.25 |

The well-known protozoan disease, coccidiosis, continues to be a serious problem and its control is of economic importance to veterinary science, especially to the poultry industry. Coccidiosis results from infection by one or more species of Eimeria or Isospora (for a summary, see Lund and Farr in "Diseases of Poultry," 5th ed., Biester and Schwarte, Eds., Iowa State University Press, Ames, Ia., 1965, pp. 1056-1096). There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively innocuous; however, *E. mitis, E. hagani* and *E. praecox* are capable of reducing weight gain, lowering feed efficiency and adversely affecting egg production.

Antibiotic CP-63,517 and its cationic salts exhibit excellent activity against coccidial infections in poultry. When incorporated into the diet of chickens at levels of 5 to 40 ppm, these compounds are effective in controlling infections due to *Eimeria tenella* and *E. acervulina*.

Efficacy data for Antibiotic CP-63,517 and its salts against coccidial infections in chickens was obtained in the following fashion. Groups of 3–5 ten-day old SPF white leghorn cockerel chicks were fed a mash diet containing Antibiotic CP-63,517, its sodium and/or potassium salt, or the known agents Monensin or Stenorol uniformly dispersed therein. After being on this ration for 24 hours each chick was inoculated per os with oocysts of the particular species of Eimeria being tested. Other groups of 3–5 ten-day old chicks were fed a similar mash diet free of any test compound. They were also infected after 24 hours and served as infected controls. Yet another group of 3–5 ten-day old chicks were fed the mash diet free of any test compound and were not infected with coccidia. These served as normal controls. The results of treatment were evaluated after five days in the case of *E. acervulina*, and six days for other challenges. Table II summarizes the results obtained.

TABLE II

| Test Compound | Species Infection | Dose (ppm) | Average Degree of Infection[1] | Ratio[1] | % Weight Gain |
|---|---|---|---|---|---|
| CP-63,517 | Eimeria tenella | 40 | 0.0 (0.0) | 0.0 (0.0) | 0 (2) |
| | | 30 | 0.0 (0.0) | 0.0 (0.0) | 0 (23) |
| | | 20 | 0.0 (0.0) | 0.0 (0.0) | 14 (26) |
| | | 10 | 0.0 (1.0) | 0.0 (0.3) | 36 (66) |
| | | 5 | 1.0 | 0.3 | 63 |
| Monensin* | Eimeria tenella | 120 | 0.3 (1.0) | 0.09 (0.32) | 71 (68) |
| | | 53 | 2.3 (1.7) | 0.69 (0.54) | 92 (99) |
| Stenorol* | Eimeria tenella | 9 | 0.0 (0.0) | 0.0 (0.0) | 63 (77) |
| | | 3 | 0.0 (0.0) | 0.0 (0.0) | 86 (103) |
| | | 0.75 | 1.7 (2.3) | 0.51 (0.73) | 66 (90) |
| CP-63,517 | Eimeria acervulina | 40 | 1.2 (1.2) | 0.60 (0.60) | 0 (0) |
| | | 30 | 0.4 (0.6) | 0.20 (0.30) | 0 (0) |
| | | 20 | 0.8 (0.4) | 0.40 (0.20) | 30 (60) |
| | | 10 | 1.0 (0.6) | 0.50 (0.30) | 40 (0) |
| | | 5 | 2.2 | 1.10 | 11 |
| Stenorol* | Eimeria acervulina | 9 | 0.0 (0.0) | 0.0 (0.0) | 48 (51) |

*Numbers in parentheses are replicate results;
Monensin, see e.g., U.S. Pat. No. 3,501,568; J. Amer. Chem. Soc., 89, 5737 (1967); Stenorol (Halofuginone), see e.g., U.S. Pat. No. 3,320,124.
[1]The criteria used to measure anticoccidial activity consisted of lesion scores of 0 to 4 for *Eimeria tenella* after J. E. Lynch, "A New Method for the Primary Evaluation of Anticoccidial Activity", Am. J. Vet. Res. 22: 324–326 (1961); and 0 to 3 for the other species based on modification of the scoring system devised by J. Johnson and W. H. Reid, "Anticoccidial Drugs. Lesion Scoring Techniques in Battery and Floor Pen Experiments in Chicks", Exp. Parasit. 28: 30–36 (1970). A constant ratio was established by dividing the lesion score of each treated group by the lesion score of the infected control.

As indicated by the data in Table I, the new antibiotic substance of this invention possesses antibacterial activity against a variety of gram-positive bacteria, such as *Staphylococcus aureus, Staphylococcus epidermidis* and *Streptococcus pyogenes*. This makes the compound of formula (I), and its salts, useful for sanitary purposes, such as the washing of hands and the sterilization of hospital surfaces and equipment.

Furthermore, the antibiotic compound of formula (I) possesses activity against *Treponema hyodysenteriae*, a microorganism which causes dysentery in swine. Accordingly, the antibiotic substance of this invention of formula (I) is useful for controlling swine dysentery. For this purpose, the compound of formula (I) can be administered to swine alone, or, preferably, in a pharmaceutical composition in which the compound of formula (I) is mixed with a pharmaceutically acceptable carrier or diluent.

Said pharmaceutical composition is prepared according to standard procedures for a veterinary antibiotic. For example, capsules can be prepared by filling gelatin capsules with the compound of formula (I), suitably diluted with an inert diluent such as glucose, lactose, sucrose, starch or cellulose. Tablets can be prepared in conventional fashion, for example, by compressing a mixture of the compound of formula (I), a diluent such as lactose or starch, a binding agent such as gelatin or guar gum, and a lubricant such as magnesium stearate or paraffin wax. Also, the compound of formula (I) can be administered orally in the form of elixers, syrups, solutions and suspensions. Solutions and suspensions can be aqueous, non-aqueous or partially aqueous. For parenteral administration, sterile, aqueous solutions are preferred. Parenteral administration includes intramuscular, intraperitoneal, subcutaneous and intravenous use. For intravenous use, the total concentration of solutes should be controlled to render the preparation isotonic.

The proportional ratio of the compound of formula (I) to the pharmaceutically acceptable carrier will depend on the dosage contemplated and the route of administration; however, said proportional ratio will normally be in the range from 1:10 to 2:1, especially 1:5 to 1:1.

Also, when using the compound of formula (I) to control swine dysentery, it is convenient to administer the compound by mixing it into the animal's feed. In this case, the compound of formula (I) will be added to the animal's feed at a level which will provide the appropriate daily dosage of the compound of formula (I).

The prescribing veterinarian will ultimately decide the dosage of the compound of formula (I) which will be administered to combat swine dysentery, and this dosage will vary according to the route of administration and the severity of the animal's symptoms. However, the compound (I) will normally be administered orally at dosages in the range from 20 to 50 milligrams per kilogram of body weight per day and 10 to 30 milligrams per kilogram of body weight per day, usually in divided doses. In some instances, it may be necessary to use dosages outside these ranges.

Yet further, the antibiotic of formula (I) of this invention and the pharmaceutically acceptable base salts thereof increase the efficiency of food utilization in swine and ruminants, i.e. they act as growth promotants. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp. 408–410. The relative efficiency of VFA utilization is discussed by McCullough in "Feedstuffs", June 19, 1971, page 19; Eskeland et al. in *J. An. Sci.*, 33, 282 (1971); and Church et al. in "Digestive Physiology and Nutrition of Ruminants," Vol. 2, 1971, pp. 622 and 625. Although acetates and butyrates are utilized, propionates are utilized with greater efficiency. A beneficial compound, therefore, stimulates animals to produce a higher proportion of propionates from carbohydrates, thereby increasing carbohydrate utilization efficiency.

The value of animal feeds generally has been determined directly by feeding the animal. British Pat. No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated calf which is fed on a commercial fattening ration plus hay. The rumen fluid is immediately filtered through cheese cloth, and 10 ml added to a 50 ml conical flask containing 400 mg of standard substrate (68% corn starch +17% cellulose +15% extracted soybean meal), 10 ml of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml of the sample is mixed with 1 ml of 25% metaphosphoric acid. After 10 minutes 0.25 ml of formic acid is added and the mixture centrifuged at 1500 RPM for 10 minutes. Samples are then analyzed by gas-liquid chromatography by the method of D. W. Kellog, *J. Dairy Science,* 52, 1690 (1969). Peak heights for acetic, propionic and butyric acids are determined for samples from untreated and treated incubation flasks.

When tested by this in vitro procedure, Antibiotic CP-63,517 at levels of 20 and 10 micrograms per milliliter gave rise to increases of 96% and 95%, respectively, in the production of propionic acid over that product in the control solution without added Antibiotic CP-63,517. By comparison the commercially available Monensin (another polycyclic ether antibiotic) at 10 μg/ml produced about 20% increase of propionic acid over the control [*J. Amer. Chem. Soc.,* 89, 5737 (1967)].

When compared with Salinomycin [*J. Antibiotics,* 27: 814 (1974)], Antibiotic CP-63,517 produced about 86% increase in propionic acid at the level of 20 μg/ml and about 66% increase at 5 μg/ml compared with the increase of about 65% for Salinomycin at 10 μg/ml.

Based on this data, it can be projected that Antibiotic CP-63,517 will improve feed utilization by ruminants such as cattle and sheep and by monogastric animals such as pigs and rabbits. Antibiotic CP-63,517 may be incorporated in feed compositions as the free acid, sodium salt, potassium salt or mixtures thereof. Crude forms of Antibiotic CP-63,517 or dried fermentation broth containing the antibiotic may be incorporated in feed compositions at the desired potency concentrations.

The following Example is provided solely for further illustration.

EXAMPLE

Isolation of Antibiotic CP-63,517 from Fermentation Broth

The whole broth of a 10 pot fermentation of culture ATCC-39574 (total volume approximately 25 liters) was extracted with one half volume of methylisobutyl ketone. The extract was concentrated in vacuo to a brown oil (20 g). This material was chromatographed on a 5×100 cm column packed with a chromatographic grade silica gel in ethyl acetate. The column was developed with ethyl acetate at a flow rate of 10 ml/minute. Fractions of 10 ml each were taken. These fractions were examined by thin-layer chromatography on silica gel plates developed in ethyl acetate. The plates were sprayed with 3% vanillin in ethanol-85% phosphoric acid (3:1) and heated to 80° C. The desired antibiotic CP-63,517 appears as a green spot under these conditions. The fractions containing CP-63,517 were combined (total volume approximately 300 ml) and stirred with 2 grams of Darco G60* carbon for 15 minutes. The mixture was filtered, and the filtrate was stirred with 300 ml of 5% sodium phosphate dibasic buffer and the pH adjusted to 10.0 with 1N NaOH. The phases were separated, and the ethyl acetate was dried over anhydrous sodium sulfate, filtered and evaporated in vacuo. The yellow viscous oil remaining after evaporation was dissolved in a small volume of acetone, whereupon crystallization occurred. The crystals were collected by filtration and dried in vacuo yielding 800 mg of CP-63,517 as the sodium salt; m.p. 215°–220° C., UV lambda(max.) 232 manometers, $E_{1\ cm}^{1\%} = 155$. Infrared spectrum (KBr) cm$^{-1}$: 3436, 2964, 2928, 2871, 2728, 1666, 1563, 1462, 1404, 1372, 1319, 1293, 1271, 1234, 1205, 1167, 1100, 1050, 1033, 995, 980, 967, 940, 926, 902, 858, 538.

Optical rotation: $[\alpha]_D = +25°$ (C=0.5, methanol).

Analysis: Calculated for $C_{47}H_{77}O_{14}Na$: C, 63.49; H, 8.89; N, 0.0. Found: C, 62.45; H, 8.61; N, 0.0.

*ICI America Inc., Wilmington, Del. 19899.

The free acid form of CP-63,517 was prepared by stirring a chloroform solution of CP-63,517 with an equal volume of water and lowering the pH to 3.0 with phosphoric acid. The phases were then separated, and the chloroform was evaporated in vacuo to give the free acid of CP-63,517 as an amorphous solid, m.p. 95°–105° C. UV lambda(max.) 232 manometers, $E_1\ cm^{1\%} = 161$. Infrared spectrum (KBr) cm$^{-1}$: 3474, 2968, 2932, 2877, 1715, 1670, 1460, 1380, 1315, 1265, 1233, 1202, 1165, 1113, 1099, 1066, 1046, 1021, 987, 950, 923, 900.

Optical rotation: $[\alpha]_D = +47.4°$ (C=0.5, methanol).

Analysis: Calculated for $C_{47}H_{78}O_{14}$: C, 65.10; H, 9.07; O, 25.83. Found: C, 64.05; H, 8.93; O, 27.03(by difference).

The structure (I) of CP-63,517 was determined by $^1$H-NMR and high resolution mass spectra studies carried out by Earl B. Whipple, PhD. and R. S. Ware, Central Research, Pfizer Inc., Groton, Conn., U.S.A.

We claim:

1. A process for producing the antibiotic of the formula:

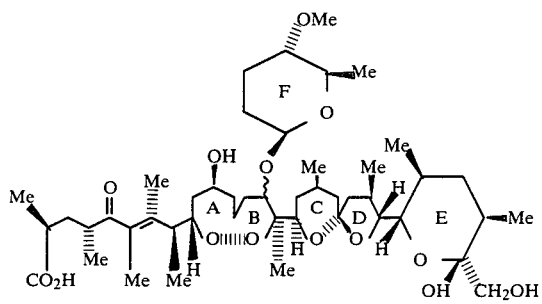

wherein Me is methyl; or a pharmaceutically acceptable cationic salt thereof, which comprises cultivating *Streptomyces endus* subsp. *aureus*, ATCC-39574, having the ability to produce said antibiotic or a pharmaceutically acceptable cationic salt thereof, in an aqueous culture medium, containing an assimilable source of carbon, nitrogen and inorganic salts, under submerged, aerobic fermentation conditions, until a recoverable amount of said antibiotic, or a pharmaceutically acceptable cationic salt thereof, is obtained, and recovering said antibiotic or pharmaceutically acceptable salt thereof.

2. The process according to claim 1, wherein said *Streptomyces endus* subsp. *aureus* is strain ATCC-39574 or a mutant thereof.

3. A biologically pure culture of a strain of the species *Streptomyces endus* subsp. *aureus*, having the identifying characteristics of ATCC-39574, said microorganism being capable of producing the antibiotic of the formula:

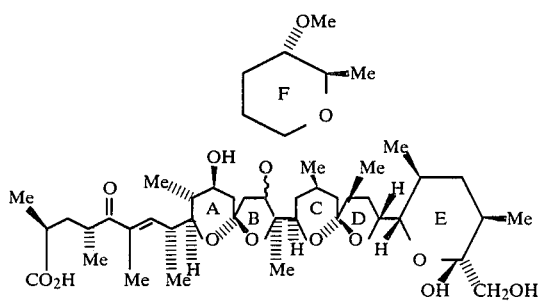

wherein Me is methyl; or a pharmaceutically acceptable cationic salt thereof, in recoverable quantity upon cultivation in an aqueous nutrient medium containing assimilable sources of carbon, nitrogen and inorganic salts.

4. The biologically pure culture of claim 3, when in freeze-dried form.

* * * * *

UNITED STATES PATENT AND TRADEMARK OFFICE
CERTIFICATE OF CORRECTION

PATENT NO. : 4,552,843

DATED : November 12, 1985

INVENTOR(S) : Walter D. Celmer, et al.

It is certified that error appears in the above-identified patent and that said Letters Patent is hereby corrected as shown below:

In the Abstract, line 3, correct the structure of formula (I) to agree with that given for (I) in columns 1 and 2.

In claim 1, at column 14, line 1, the formula should be corrected to agree with that given for (I) in columns 1 and 2.

In claim 3, at column 14, line 35, the formula should be corrected to agree with that given for (I) in columns 1 and 2.

Signed and Sealed this

Eleventh Day of March 1986

[SEAL]

Attest:

DONALD J. QUIGG

Attesting Officer

Commissioner of Patents and Trademarks